(12) United States Patent
Nakamura

(10) Patent No.: US 10,371,746 B2
(45) Date of Patent: Aug. 6, 2019

(54) HEAT GENERATION POINT DETECTION METHOD AND HEAT GENERATION POINT DETECTION DEVICE

(71) Applicant: HAMAMATSU PHOTONICS K.K., Hamamatsu-shi, Shizuoka (JP)

(72) Inventor: Tomonori Nakamura, Hamamatsu (JP)

(73) Assignee: HAMAMATSU PHOTONICS K.K., Hamamatsu-shi, Shizuoka (JP)

( * ) Notice: Subject to any disclaimer, the term of this patent is extended or adjusted under 35 U.S.C. 154(b) by 0 days.

(21) Appl. No.: 15/402,590

(22) Filed: Jan. 10, 2017

(65) Prior Publication Data

US 2017/0123004 A1 May 4, 2017

Related U.S. Application Data

(63) Continuation of application No. 14/232,021, filed as application No. PCT/JP2012/067706 on Jul. 11, 2012, now Pat. No. 9,575,020.

(30) Foreign Application Priority Data

Jul. 13, 2011 (JP) ................................ 2011-154855

(51) Int. Cl.
*H01L 23/34* (2006.01)
*G01R 31/311* (2006.01)
*G01N 25/72* (2006.01)

(52) U.S. Cl.
CPC ........... *G01R 31/311* (2013.01); *G01N 25/72* (2013.01); *H01L 23/34* (2013.01); *H01L 2924/0002* (2013.01)

(58) Field of Classification Search
None
See application file for complete search history.

(56) References Cited

U.S. PATENT DOCUMENTS 6,812,468 B1 11/2004 Baumann et al.
7,401,976 B1 7/2008 Schlagheck et al.
(Continued)

FOREIGN PATENT DOCUMENTS

CN 1395112 2/2003
JP H3-156351 7/1991
(Continued)

OTHER PUBLICATIONS

C. Schmidt, et al., Lock-in-Thermography for 3-dimensional localization of electrical defects inside complex packaged devices, ISTFA 2008: Proceedings from the 34th International Symposium for Testing and Failure Analysis, Nov. 2008, pp. 102-107.
(Continued)

*Primary Examiner* — Erica S Lin
(74) *Attorney, Agent, or Firm* — Drinker Biddle & Reath LLP

(57) ABSTRACT

A heat generation point detection method comprises steps S01, S02 of applying a low frequency bias voltage to an integrated circuit S and acquiring a heat generation detection signal detected from the integrated circuit S in response thereto, steps S03, S04 of supplying a high frequency bias voltage to the integrated circuit S and acquiring a heat generation detection signal detected from the integrated circuit S in response thereto, steps S05 to S07 of detecting a phase shift between the low frequency bias voltage and the heat generation detection signal and a phase shift between the high frequency bias voltage and the heat generation detection signal, and a step S08 of calculating a change rate of the phase shift against a square root of the frequency of the bias voltage, based on those phase shifts, and acquiring depth information of a heat generation point from the change rate.

14 Claims, 6 Drawing Sheets

(56) References Cited

U.S. PATENT DOCUMENTS

| | | |
|---|---|---|
| 2006/0274151 A1 | 12/2006 | Lueerssen et al. |
| 2009/0297017 A1 | 12/2009 | Hudgings et al. |
| 2010/0062550 A1 | 3/2010 | Buchel et al. |
| 2011/0297829 A1* | 12/2011 | Altmann .................. G01N 1/00 250/332 |

FOREIGN PATENT DOCUMENTS

| | | |
|---|---|---|
| JP | H06-207914 A | 7/1994 |
| JP | H06-265496 A | 9/1994 |
| JP | H11-337511 A | 12/1999 |
| JP | 2003-035690 A | 2/2003 |
| JP | 2005-241573 | 9/2005 |
| JP | 2005-291791 A | 10/2005 |
| JP | 2007-024674 A | 2/2007 |
| JP | 2008-545232 | 12/2008 |
| JP | 2013-526723 | 6/2013 |
| TW | 200707719 | 2/2007 |
| WO | WO 2005/005972 | 1/2005 |

OTHER PUBLICATIONS

Schmidt, Christian, et al., "Localization of Electrical Defects in System in Package Devices Using Lock-in Thermography," Electronic System-Integration Technology Conference (ESTC), 2010 3rd, IEEE, Piscataway, NJ, USA, Sep. 13, 2010, pp. 1-5.

Schmidt, Christian, et al., "Non-Destructive Defect Depth Determination at Fully Packaged and Stacked Die Devices using Lock-in Thermography," Physical and Failure Analysis of Integrated Circuits (IPFA), 2010 17th IEEE International Symposium on the, IEEE, Piscataway, NJ, USA, Jul. 5, 2010, pp. 1-5.

U.S. Office Action dated Apr. 21, 2016 that issued in U.S. Appl. No. 14/355,596 including Double Patenting Rejections on pp. 2-4.

* cited by examiner

HEAT GENERATION POINT DETECTION METHOD AND HEAT GENERATION POINT DETECTION DEVICE

This is a continuation application of copending application Ser. No. 14/232,021, having a § 371 date of Feb. 4, 2014, which is a national stage filing based on PCT International Application No. PCT/JP2012/067706, filed on Jul. 11, 2012. The copending application Ser. No. 14/232,021 is incorporated by reference herein in its entirety.

TECHNICAL FIELD

The present invention relates to a heat generation point detection method and a heat generation point detection device for detecting a depth of a heat generation point in an integrated circuit.

BACKGROUND ART

A method of applying a periodic pulse voltage to an integrated circuit and detecting a thermal response is known as a conventional failure analysis method for integrated circuits such as LSI packages. For example, Non Patent Literature 1 below describes that a phase shift $\Delta\Phi$ between electrical excitation and a local thermal response is detected and a depth of a defect is determined from the phase shift $\Delta\Phi$.

CITATION LIST

Non Patent Literature

Non Patent Literature 1: C. Schmidt et al., "Lock-in-Thermography for 3-dimensional localization of electrical defects inside complex packaged devices," ISTFA2008: Proceedings from the 34th International Symposium for Testing and Failure Analysis, U.S.A., November 2008, p. 102-107.

SUMMARY OF INVENTION

Technical Problem

In the above-described conventional analysis method, however, the phase shift $\Delta\Phi$ is dependent on an amount of heat generation, a structure of an integrated circuit, and a position of a defect point, as well as the depth of the defect point because the amount of heat generation varies depending upon the amplitude of an excitation signal and the condition of the defect point and because the heat capacity between the defect point and the surface of the integrated circuit varies depending upon the position of the defect point. Therefore, when the depth of the defect was evaluated from the phase shift $\Delta\Phi$, an error of an evaluated value thereof tended to become larger.

Under such circumstances, the present invention has been accomplished in view of the foregoing problem and it is an object of the present invention to provide a heat generation point detection method and a heat generation point detection device allowing accurate detection of a depth of a heat generation point in an integrated circuit, independent of the condition and position thereof.

Solution to Problem

In order to solve the above problem, a heat generation point detection method according to an aspect of the present invention is a heat generation point detection method for detecting a depth of a heat generation point in an integrated circuit, comprising: a first step of supplying a periodic electric signal fluctuating at a first frequency, to the integrated circuit and acquiring a first detection signal indicative of a change of an amount of heat generation detected from the integrated circuit in response thereto; a second step of supplying a periodic electric signal fluctuating at a second frequency different from the first frequency, to the integrated circuit and acquiring a second detection signal indicative of a change of an amount of heat generation detected from the integrated circuit in response thereto; a third step of detecting a first phase shift between the periodic electric signal of the first frequency and the first detection signal and a second phase shift between the periodic electric signal of the second frequency and the second detection signal; and a fourth step of calculating a change rate of the phase shift between the periodic electric signal and the detection signal against a variable calculated from the frequency of the periodic electric signal, based on the first and second phase shifts, and acquiring depth information of the heat generation point from the change rate.

Furthermore, a heat generation point detection device according to another aspect of the present invention is a heat generation point detection device for detecting a depth of a heat generation point in an integrated circuit, comprising: an electric signal supply unit for supplying an electric signal to the integrated circuit; a control unit for controlling the electric signal supply unit so as to supply a periodic electric signal fluctuating at a first frequency and a periodic electric signal fluctuating at a second frequency different from the first frequency, to the integrated circuit; a detection unit for acquiring a first detection signal indicative of a change of an amount of heat generation detected from the integrated circuit in response to supply of the periodic electric signal of the first frequency and acquiring a second detection signal indicative of a change of an amount of heat generation detected from the integrated circuit in response to supply of the periodic electric signal of the second frequency; a phase shift detection unit for detecting a first phase shift between the periodic electric signal of the first frequency and the first detection signal and a second phase shift between the periodic electric signal of the second frequency and the second detection signal; and a calculation unit for calculating a change rate of the phase shift between the periodic electric signal and the detection signal against a variable calculated from the frequency of the periodic electric signal, based on the first and second phase shifts, and acquiring depth information of the heat generation point from the change rate.

The heat generation point detection method or the heat generation point detection device is configured to detect the first detection signal indicative of the change of the amount of heat generation in response to the supply of the periodic electric signal of the first frequency and detect the second detection signal indicative of the change of the amount of heat generation in response to the supply of the periodic electric signal of the second frequency, from the integrated circuit. Then the first phase shift between the periodic electric signal of the first frequency and the first detection signal and the second phase shift between the periodic electric signal of the second frequency and the second detection signal are detected and the depth information of the heat generation point is obtained from the change rate of the phase shift against the variable calculated from the frequency of the periodic electric signal. This procedure is to calculate the depth information while cancelling out an offset component in the temporal change of the amount of heat generation varying depending upon the position of the heat generation point; therefore, the depth information is obtained with high accuracy, independent of the position of the heat generation point. By acquiring the change rate of the phase shift against the variable calculated from the frequency of the periodic electric signal, we can also obtain the depth information independent of the amount of heat generation at the heat generation point, the internal structure of the integrated circuit, and the frequency of the periodic electric signal.

Advantageous Effect of Invention

The present invention allows accurate detection of the depth of the heat generation point in the integrated circuit, independent of the condition and position thereof.

DESCRIPTION OF EMBODIMENTS

The preferred embodiments of the heat generation point detection device according to the present invention and the heat generation point detection method using the same will be described below in detail with reference to the drawings. Identical or equivalent portions will be denoted by the same reference signs in the description of the drawings, without redundant description.

Figure 1:
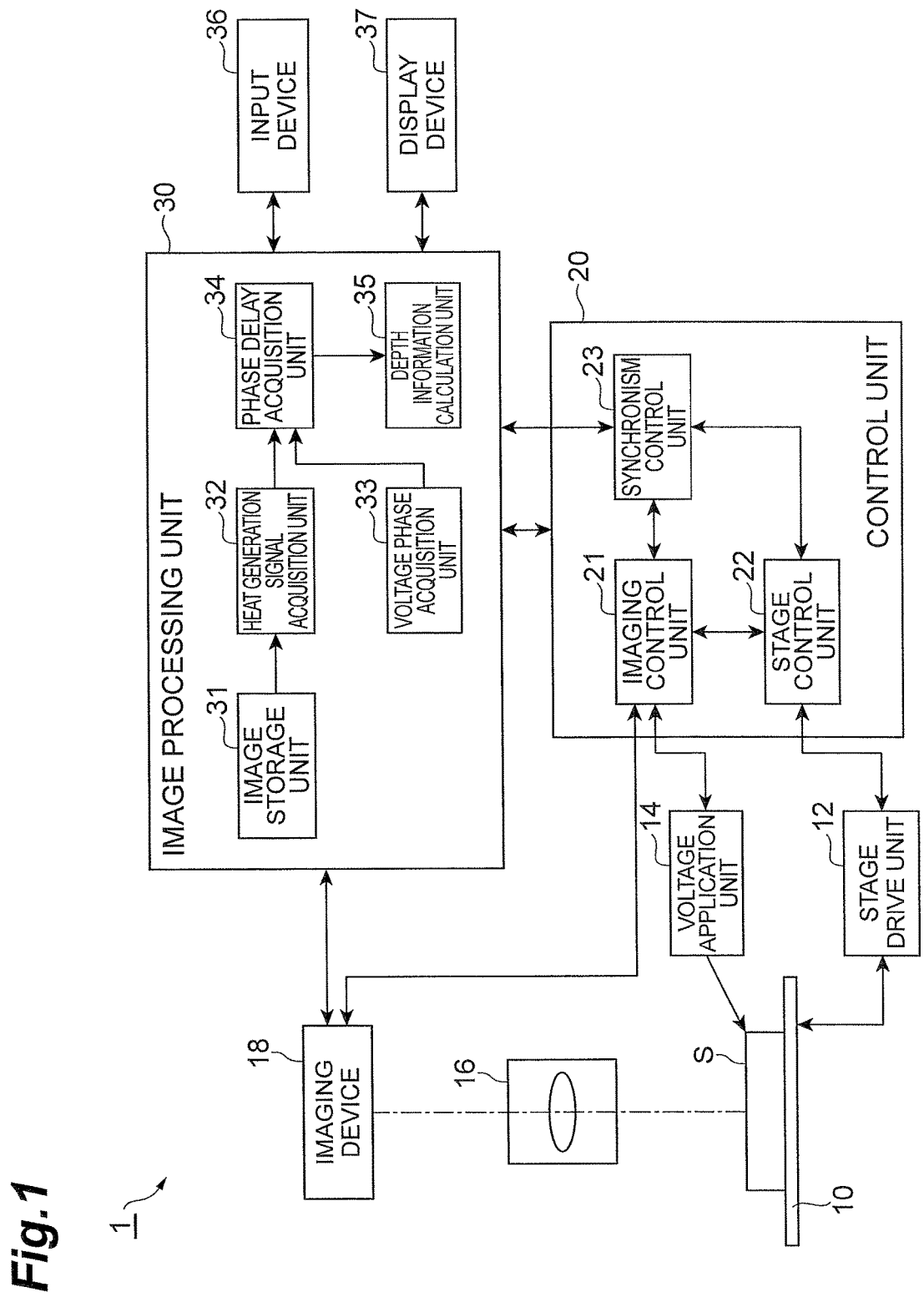
FIG. 1 is a block diagram showing a schematic configuration of an integrated circuit failure analysis device according to a preferred embodiment of the present invention.

FIG. 1 is a block diagram showing a schematic configuration of an integrated circuit failure analysis device which is a heat generation point detection device according to a preferred embodiment of the present invention. The integrated circuit failure analysis device 1 shown in the same drawing is a failure analysis device which detects a position of a heat generation point in an integrated circuit S such as an LSI package and performs a failure analysis. This integrated circuit failure analysis device 1 is configured with a sample stage 10, a stage drive unit 12 to drive the sample stage 10, a voltage application unit (electric signal supply unit) 14, an imaging device 18, a control unit 20, and an image processing unit 30.

The integrated circuit S as an analysis target is mounted on the sample stage 10 using X-, Y-, and Z-stages which can be driven in X-axis direction, Y-axis direction (horizontal direction), and Z-axis direction (vertical direction), respectively. This sample stage 10 is configured so that it can be driven in the X-, Y-, and Z-directions by the stage drive unit 12, thereby to carry out focusing in imaging, position alignment of imaging position, and so on for the integrated circuit S. The imaging device 18 as imaging means for acquiring a two-dimensional image of the integrated circuit S is installed above the sample stage 10. The imaging device 18 to be suitably used herein is an imaging device sensitive to a predetermined wavelength region, for acquiring an image based on a heat generation image on the surface of the integrated circuit S, e.g., an infrared imaging device sensitive to the infrared wavelength region.

A light-guide optical system 16 such as an objective lens for guiding the image on the surface of the integrated circuit S to the imaging device 18 is disposed on the optical axis between the sample stage 10 and the imaging device 18. The integrated circuit failure analysis device may be configured as follows: the light-guide optical system 16 is provided with a driving mechanism such as X-, Y-, and Z-stages and this driving mechanism allows the device to implement the focusing in imaging, the position alignment of imaging position, and so on for the integrated circuit S.

The integrated circuit failure analysis device is provided with the voltage application unit 14 for supplying a voltage signal to the integrated circuit S on the sample stage 10. The voltage application unit 14 is voltage application means for applying a necessary bias voltage to an electronic circuit in the integrated circuit S in carrying out a failure analysis based on detection of a heat generation point, and is configured including a power supply for application of voltage. Specifically, the voltage application unit 14 applies a voltage signal (periodic electric signal) of a rectangular wave fluctuating periodically, as a bias voltage. This operation results in applying a high voltage and a low voltage periodically to the integrated circuit S. The voltage application unit 14 is configured so that the frequency (repetition period) of the applied bias voltage can be changed by control of the control unit 20. The voltage application unit 14 is configured so that values of the high voltage and low voltage of the applied bias voltage can be changed by control of the control unit 20.

The imaging device 18 acquires a plurality of analysis images in time series in a state in which the bias voltage is applied to the integrated circuit S by the voltage application unit 14. The analysis images acquired in this manner are images including the heat generation image on the surface of the integrated circuit S. The imaging frequency (frame rate) of the imaging device 18 may be set based on the frequency of the bias voltage applied to the integrated circuit S by the voltage application unit 14. For example, the imaging frequency of the imaging device 18 may be the same period as the frequency of the bias voltage applied to the integrated circuit S or may be set in proportion to the frequency of the bias voltage. This setting allows the device to acquire heat generation images in relatively identical heat generation conditions, even at different frequencies of bias voltages.

Furthermore, for these sample stage 10, stage drive unit 12, voltage application unit 14, light-guide optical system 16, and imaging device 18, the integrated circuit failure analysis device 1 is provided with a control unit 20 for controlling operations thereof. This control unit 20 is configured with an imaging control unit 21, a stage control unit 22, and a synchronism control unit 23.

The imaging control unit 21 controls the bias voltage application operation by the voltage application unit 14 and the image acquisition operation by the imaging device 18, thereby to control the acquisition of analysis images of the integrated circuit S. The stage control unit 22 controls the operation of the sample stage 10 and the stage drive unit 12 (the moving operation of the integrated circuit S on the sample stage 10). The synchronism control unit 23 performs a control for achieving necessary synchronism of the imaging control unit 21 and the stage control unit 22 with the image processing unit 30 provided for the imaging device 18. Namely, the synchronism control unit 23 controls the stage control unit 22 to move the stage to a predetermined position for execution of a failure analysis of the integrated circuit S and thereafter controls the imaging control unit 21 to change frequencies of bias voltages at predetermined intervals in order. The synchronism control unit 23 also controls the value of the high voltage and the value of the low voltage in the bias voltage applied periodically. The synchronism control unit 23 controls the imaging control unit 21 to separately acquire the analysis images of the integrated circuit S in time with change timings of the frequencies of the bias voltages.

The image processing unit 30 is image processing means for performing image processing necessary for the failure analysis of the integrated circuit S, on the images acquired by the imaging device 18. The image processing unit 30 in the present embodiment is configured with an image storage unit 31, a heat generation signal acquisition unit (detection unit) 32, a voltage phase acquisition unit 33, a phase delay acquisition unit (phase shift detection unit) 34, and a depth information calculation unit 35. The images of the integrated circuit S acquired by the imaging device 18 are fed to the image processing unit 30 and stored and accumulated in the image storage unit 31 as occasion may demand.

The heat generation signal acquisition unit 32 acquires a heat generation detection signal indicative of a temporal change of an amount of heat generation detected at a plurality of points on the surface of the integrated circuit S, based on the plurality of analysis images acquired in time series.

The voltage phase acquisition unit 33 receives the waveform of the bias voltage applied by the voltage application unit 14, from the synchronism control unit 23, and acquires information of the phase of the bias voltage. The information of the phase of the bias voltage may be acquired by the voltage application unit 14 or by the control unit 20 and then supplied to the voltage phase acquisition unit 33 therefrom.

The phase delay acquisition unit 34 acquires information of the phase of a heat generation detection signal with respect to the information of the phase of the bias voltage applied by the voltage application unit 14, based on the heat generation detection signal indicative of the temporal change of the amount of heat generation acquired by the heat generation signal acquisition unit 32 and the phase information acquired by the voltage phase acquisition unit 33. This information of the phase of the heat generation detection signal corresponds to a phase shift between the bias voltage and the heat generation detection signal detected upon application of the bias voltage and, specifically, the phase delay acquisition unit 34 calculates a difference between the phase of the heat generation detection signal acquired by the heat generation signal acquisition unit 32 and the phase information acquired by the voltage phase acquisition unit 33. Here, the phase delay acquisition unit 34 detects the phase shift between the bias voltage and the heat generation detection signal, for each of the bias voltages changed to a plurality of frequencies. The phase delay acquisition unit 34 may directly acquire the phase shift by lock-in processing, from objects of the waveform of the heat generation detection signal and the waveform of the bias voltage. In this case, an output signal about the phase shift can be acquired by feeding the heat generation detection signal and the bias signal to a lock-in detector.

The depth information calculation unit 35 calculates the depth information of the heat generation point in the integrated circuit S, based on a plurality of phase shifts corresponding to the bias voltages of a plurality of frequencies, which were detected by the phase delay acquisition unit 34. Namely, the depth information calculation unit 35 calculates a change rate of the phase shift against a square root of the frequency which is a variable calculated from the frequency of the bias voltage, and calculates as the depth information the change rate or a value obtained by multiplying the change rate by a predetermined constant. This predetermined constant is preliminarily set as a coefficient about heat transfer dependent on physical properties of a material of the integrated circuit S. The depth information calculated in this manner indicates the depth of the heat generation point detected over a plurality of points in the integrated circuit S and is used for the failure analysis of the integrated circuit S.

The image processing unit 30 of this configuration is constructed, for example, using a computer. An input device 36 and a display device 37 are connected to this image processing unit 30. The input device 36 is composed, for example, of a keyboard, a mouse, and so on and is used, for example, to enter information and operation instructions necessary for execution of the image acquisition operation and the failure analysis operation in the integrated circuit failure analysis device 1. The display device 37 is composed, for example, of a CRT display, a liquid crystal display, or the like and is used, for example, to display various kinds of information such as the images and the depth information about the failure analysis in the integrated circuit failure analysis device 1.

This image processing unit 30 may be configured so that it, together with the control unit 20, is implemented as a single control device (e.g., a single computer). Concerning the input device 36 and the display device 37 connected to the image processing unit 30, they may also be configured similarly so as to function as input device and display device connected not only to the image processing unit 30 but also to the control unit 20.

Figure 2:
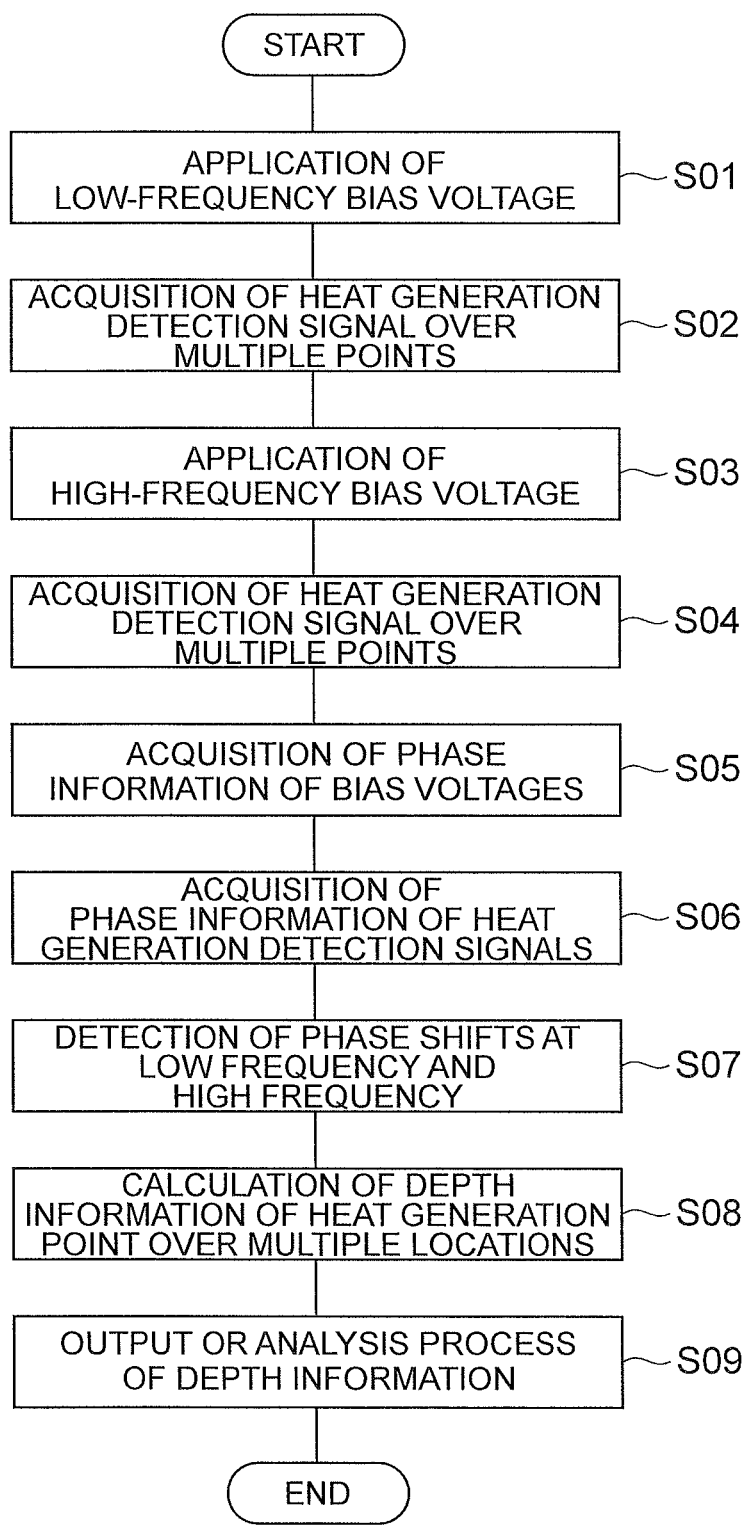
FIG. 2 is a flowchart showing a procedure of a failure analysis operation for an integrated circuit S by the integrated circuit failure analysis device 1 in FIG. 1.
Figure 4:
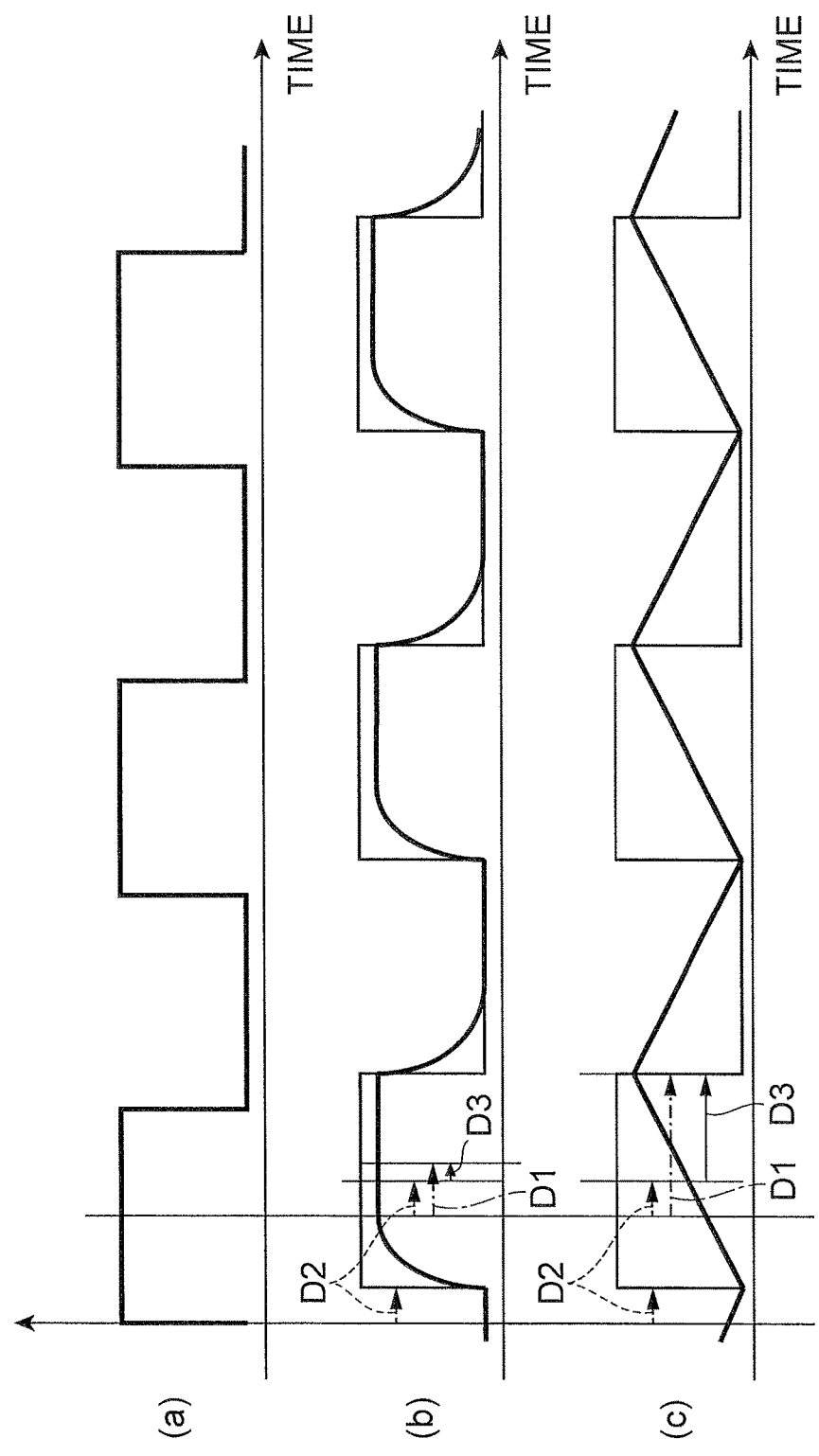
FIG. 4 is a drawing wherein (a) shows a temporal change of a bias voltage, (b) a temporal change of a heat generation detection signal detected in an integrated circuit S comprised of a material with low heat capacity/low heat transfer coefficient, and (c) a temporal change of a heat generation detection signal detected in an integrated circuit S comprised of a material with high heat capacity/high heat transfer coefficient.
Figure 5:
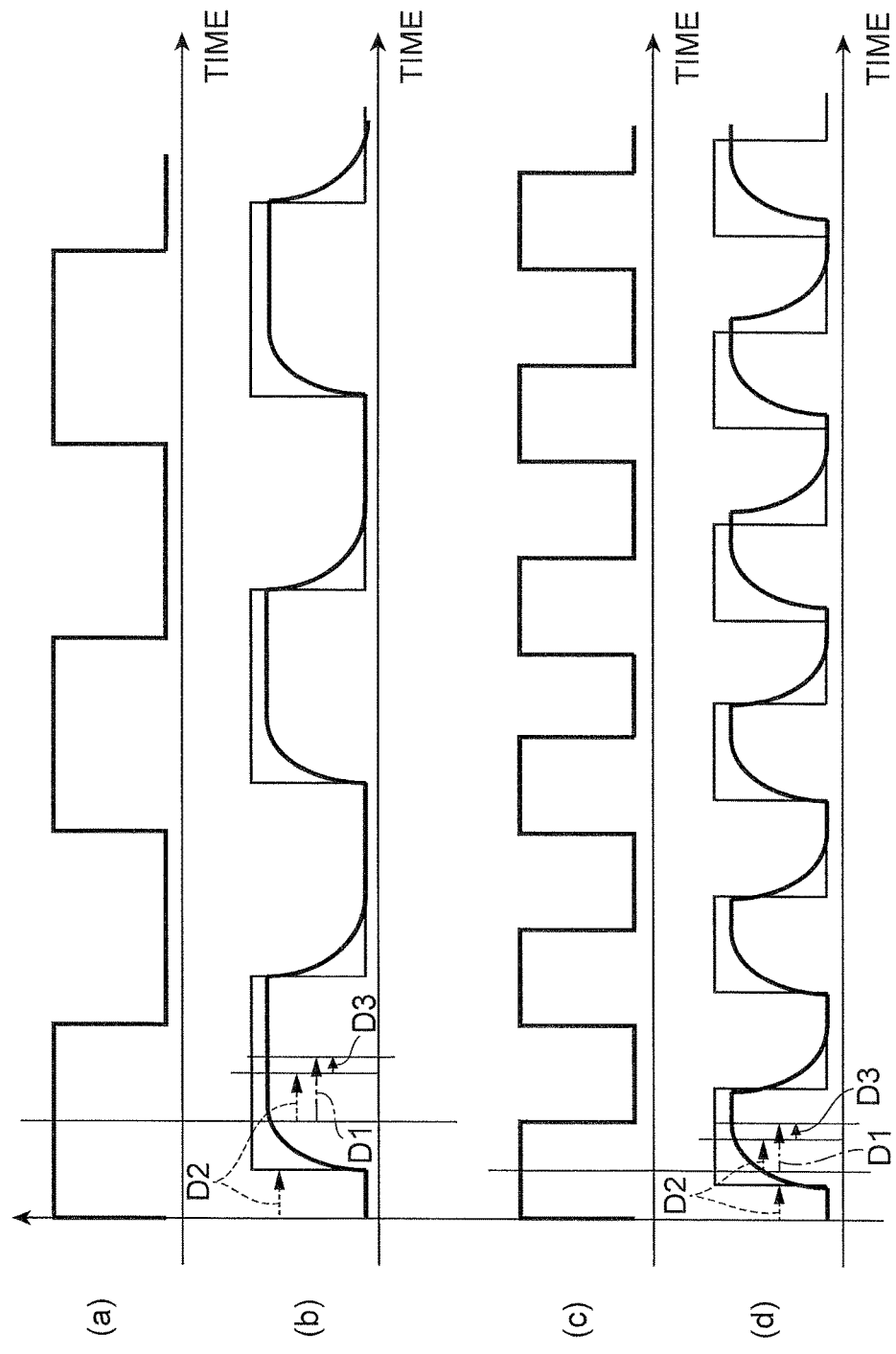
FIG. 5 is a drawing wherein (a) shows a temporal change of a bias voltage applied at a low frequency, (b) a temporal change of a heat generation detection signal detected in the integrated circuit S, (c) a temporal change of a bias voltage applied at a high frequency, and (d) a temporal change of a heat generation detection signal detected in the integrated circuit S.

The following will describe the procedure of the failure analysis operation about the integrated circuit S by the integrated circuit failure analysis device 1 and detail the heat generation point detection method according to the present embodiment. FIG. 2 is a flowchart showing the procedure of the failure analysis operation about the integrated circuit S by the integrated circuit failure analysis device 1, and FIGS. 3 to 5 are drawings showing temporal changes of signal waveforms processed in the failure analysis operation by the integrated circuit failure analysis device 1.

First, the synchronism control unit 23 controls the voltage application unit 14 to apply a bias voltage fluctuating at a low frequency (e.g., 1 Hz), to the integrated circuit S (step S01). This control causes a high voltage and a low voltage to be applied periodically to the integrated circuit S. In conjunction therewith, the imaging control unit 21 controls the imaging device 18 to separately acquire images according to the application timing of the low-frequency bias voltage. For example, the imaging control unit 21 controls the imaging device 18 to take images at the same frequency as the low frequency applied to the integrated circuit S or at an imaging frequency (frame rate) proportional to the low frequency. The images of the integrated circuit S acquired in this manner are stored once into the image storage unit 31 and thereafter processed by the heat generation signal acquisition unit 32, thereby to acquire a heat generation detection signal indicative of a temporal change of an amount of heat generation at a plurality of points (step S02).

Next, the synchronism control unit 23 controls the voltage application unit 14 to apply a bias voltage fluctuating at a high frequency (e.g., 2 Hz), to the integrated circuit S (step S03). This control causes a high voltage and a low voltage to be applied periodically to the integrated circuit S. In conjunction therewith, the imaging control unit 21 controls the imaging device 18 to separately acquire images according to the application timing of the high-frequency bias voltage. For example, the imaging control unit 21 controls the imaging device 18 to take images at the same frequency as the high frequency applied to the integrated circuit S or at an imaging frequency (frame rate) proportional to the high frequency. The images of the integrated circuit S acquired in this manner are stored once into the image storage unit 31 and thereafter processed by the heat generation signal acquisition unit 32, thereby to acquire a heat generation detection signal at a plurality of points (step S04). The frequencies of the bias voltages applied in steps S01, S03 may be suitably changed but are preferably set to not more than 10 Hz because too high frequencies must lead to place dependency of heat transference and amount of heat generation. The frequencies of the bias voltages changed do not always have to be limited to two types, but may be three or more types to acquire heat generation detection signals according thereto.

Figure 3:
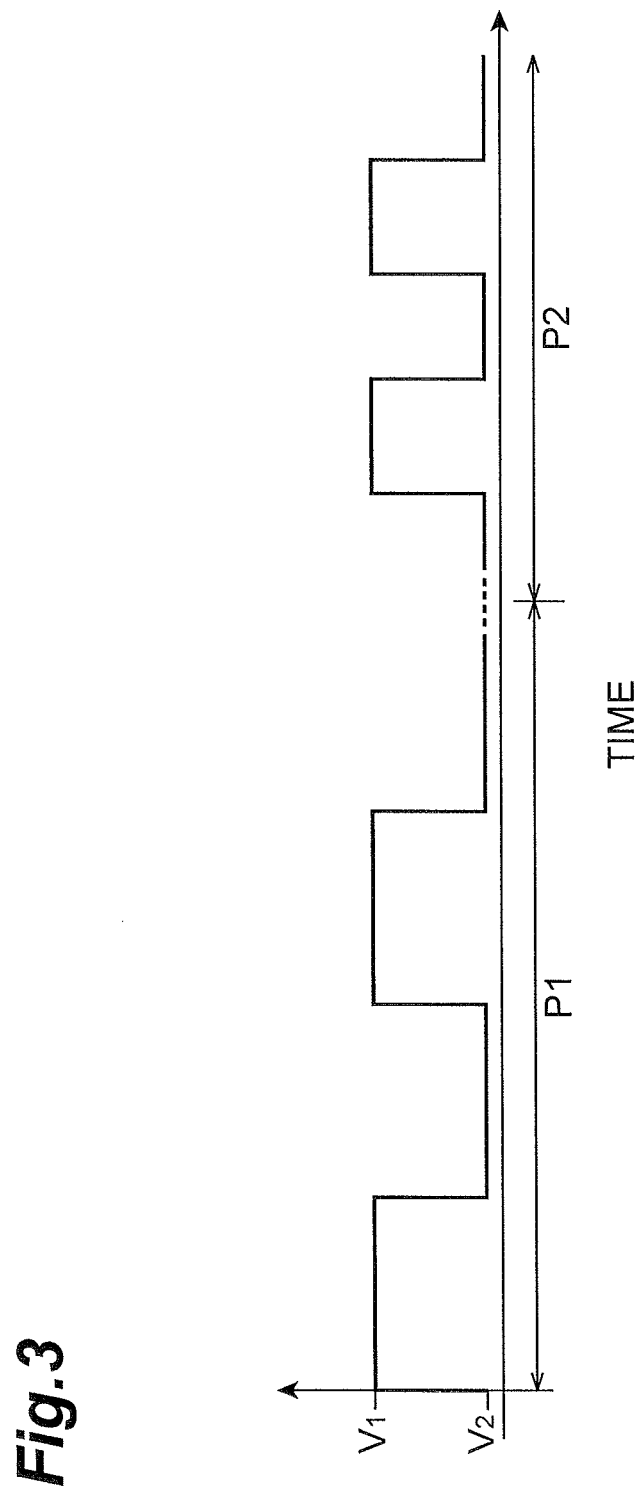
FIG. 3 is a drawing showing a temporal change of bias voltages applied by a voltage application unit 14 in FIG. 1.

FIG. 3 shows a temporal change of the bias voltages applied in steps S01, S03. As shown in the same drawing, the synchronism control unit 23 controls the bias voltages so that a high-frequency period P2 follows a low-frequency period P1 in series and, a duration of acquisition of the heat generation detection signal in each of the period P1 and the period P2 is set so that a certain length of time passes after a start of application of the bias voltage in each of the periods P1, P2, in order to make the temperature in the integrated circuit S constant between those durations so as not to affect the amount of heat generation. It is also permissible to place a period without application of voltage between the period P1 and the period P2. The maximum voltages $V_1$ and minimum voltages $V_2$ of the bias voltages of rectangular waves are set at respective identical values between the frequencies so as to equalize conditions during heat generation in the integrated circuit S and the duty ratios of the bias voltages are also set at an identical value (e.g., 50%, 75%, . . . ) between the frequencies so as to equalize amounts of heat generation in the integrated circuit S. This is for keeping an average temperature of a sample constant by making the amount of heat generation constant in the integrated circuit S. In this case, it is also possible to set the durations of acquisition of heat generation detection signals in the period P1 and in the period P2 continuous.

Referring back to FIG. 2, from targets of the waveforms of the low-frequency and high-frequency bias voltages applied to the integrated circuit S in steps S01, 03, the voltage phase acquisition unit 33 then acquires the phase information thereof (step S05).

Next, from processing targets of the heat generation detection signals corresponding to the application of the low-frequency and high-frequency bias voltages, which were acquired in steps S02, S04, the phase delay acquisition unit 34 acquires the phase information thereof with respect to the information of the phases of the bias voltages acquired in step S05 and detects phase shifts of the respective heat generation detection signals (steps S06, S07). Specifically, the phase delay acquisition unit 34 detects the phase shift from the heat generation detection signal about each of the low-frequency and high-frequency bias voltages, based on the heat generation detection signals corresponding to the application of the low-frequency and high-frequency bias voltages, which were acquired in steps S02, S04, and based on the information of the phases of the waveforms of the low-frequency and high-frequency bias voltages applied to the integrated circuit S in steps S01, 03. Next, the depth information calculation unit 35 calculates a change rate of the phase shift against the square root of the frequency, based on the phase shifts corresponding to the two frequencies, and multiplies the change rate by a predetermined constant to obtain the depth information (step S08). This depth information is calculated over a plurality of points on the surface of the integrated circuit S. Finally, the depth information thus calculated is processed as failure analysis information and displayed on the display device 37 (step S09).

The below will describe a mechanism of detection of the depth information of a heat generation point by the integrated circuit failure analysis device 1.

In FIG. 4, (a) shows a temporal change of a bias voltage applied at a certain frequency, (b) a temporal change of a heat generation detection signal detected in the integrated circuit S comprised of a material with low heat capacity/low heat transfer coefficient in response thereto, and (c) a temporal change of a heat generation detection signal detected in the integrated circuit S comprised of a material with high heat capacity/high heat transfer coefficient in response thereto. A phase shift calculated by the phase delay acquisition unit 34 in the integrated circuit failure analysis device 1 is D1 and this phase shift D1 includes a phase shift component D2 determined by a depth of a heat generation point in the integrated circuit S and a phase shift component D3 due to differences of delay of heat generation, heat capacity, and heat transfer rate. The shift component D3 in the phase shift D1 is significantly affected by a material of a heat transfer path in the integrated circuit S.

This difference of the phase shift D1 depending on the material can be explained as follows. A quantity Q of heat one-dimensionally transferred from the interior of the integrated circuit S is represented by Expression (1) below;

[Math 1]

$$Q = 1 + \exp\{-ax + i(wt - bx)\} \quad (1)$$

In this expression, x represents a distance from a heat generation source to an observation point (surface) (=depth of the heat generation point), Q a quantity of heat passing the observation point, w the angular frequency (½π Hz), b a phase delay per unit length, and a an attenuation rate per unit length. A temperature T against this heat quantity Q is represented as changing quantity by Expression (2) below;

[Math 2]

$$dT = -\frac{1}{\rho q}\frac{dQ}{dx}, \quad (2)$$

where q represents the specific heat and ρ the density.

Furthermore, from the thermal diffusion equation, where the heat transfer coefficient is denoted by κ, Expression (3) below is derived;

[Math 3]

$$\frac{dQ}{dt} = iw(Q-1) = \kappa \frac{d^2T}{dx^2}. \quad (3)$$

From Expressions (2) and (3), Expression (4) below is derived.

[Math 4]

$$Q - 1 = -i\left(\frac{\kappa}{w\rho q}\right)\frac{d^2Q}{dx^2} \quad (4)$$

The second derivative of Q with respect to x is derived from Expression (1), to obtain Expression (5) below;

[Math 5]

$$\frac{d^2Q}{dx^2} = (a+ib)^2(Q-1), \quad (5)$$

and from Expressions (4) and (5), Expression (6) below is further derived;

[Math 6]

$$(a+ib)^2 = -i\left(\frac{w\rho q}{\kappa}\right). \quad (6)$$

Since the square root of imaginary i is (1+i)/√2, Expression (6) is modified into Expression (7) below;

[Math 7]

$$a + ib = \pm\frac{1+i}{\sqrt{2}}\sqrt{\frac{\rho qw}{\kappa}}. \quad (7)$$

By expanding the above Expression (7), the attenuation constant a and the proportionality constant b of phase delay amount are expressed as Expression (8) below;

[Math 8]

$$a = b = \sqrt{\frac{\rho qw}{2\kappa}} = \sqrt{f}\sqrt{\frac{\rho q\pi}{\kappa}}. \quad (8)$$

It is, however, noted that the above relation excludes the signs indicative of opposite heat flows. As a matter of fact, the phase delay quantity can have an offset due to occurrence of distortion of waveform if there is a nonlinear factor such as transfer of heat through a plurality of paths, e.g., reflection from the sample edge, or slower heat transfer from the surface to the atmosphere than inside the sample, in actual measurement.

The conventional technology was to consider that the phase delay bx of heat generation observed at an observation point (surface) was proportional to the depth, and to simply calculate the depth of the heat generation source, based thereon. However, the offset can be produced in the actual delay quantity. This is dependent on the heat capacity inside the integrated circuit S, the amount of heat generation, the shape, the frequency of applied bias, and so on. For this reason, the phase offset varies depending upon where observation is conducted in the integrated circuit S, and it is difficult to always calculate an accurate depth of the heat generation source by the conventional technology. In contrast to it, the heat generation point detection method according to the present embodiment makes use of the finding that, as to the heat generation detection signals from the interior of the package of the integrated circuit S, the phase offset has little change against the square root of the frequency, at the low frequencies of the applied biases of not more than several Hz. The frequencies applicable herein have an upper limit value varying depending upon the integrated circuit S and are preferably not more than 4 Hz.

Namely, the depth information detected in the heat generation point detection method according to the present embodiment is a slope of the phase delay bx against the square root of the frequency, and is a value represented by Expression (9) below;

[Math 9]

$$\frac{dbx}{d\sqrt{f}} = x\sqrt{\frac{\rho q\pi}{\kappa}}. \quad (9)$$

This value is dependent on only the constants ρ, q, and κ determined by physical properties, and the constant π, successfully excluding the influence of the phase offset.

In FIG. 5, (a) shows a temporal change of a bias voltage applied at a low frequency of 1 Hz, (b) a temporal change of a heat generation detection signal detected in the integrated circuit S in response thereto, (c) a temporal change of a bias voltage applied at a high frequency of 2 Hz, and (d) a temporal change of a heat generation detection signal detected in the integrated circuit S in response thereto. In the integrated circuit failure analysis device 1, a delay corresponding to the phase delay bx is observed as a delay quantity D1 at each frequency. This delay quantity D1 includes a phase shift component D2 determined by a depth of a heat generation point and a phase shift component D3 determined by the shape of the interior of a sample, the condition of the surface, and so on.

Figure 6:
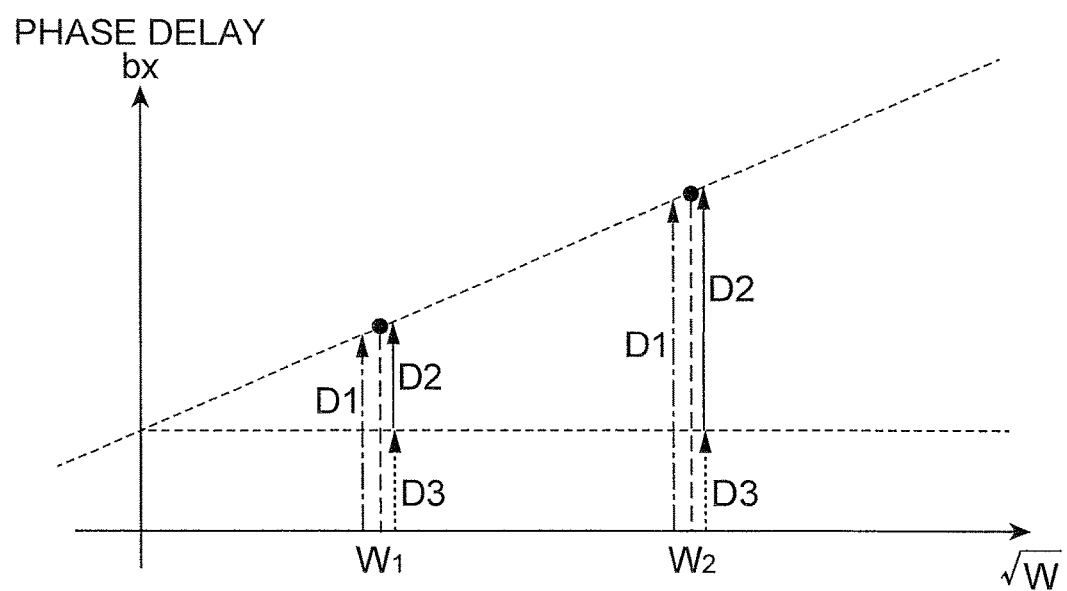
FIG. 6 is a graph showing a relationship between a square root of angular frequency of bias voltages applied to the integrated circuit S and observed phase delay bx, in the integrated circuit failure analysis device in FIG. 1.

FIG. 6 shows a relationship between the square root of the angular frequency w of the bias voltage applied to the integrated circuit S and the observed phase delay bx, in the integrated circuit failure analysis device 1. As shown in the same drawing, each of the phase delays D1 observed at the low angular frequency $w_1$ and at the high angular frequency $w_2$ includes the shift component D2 and the shift component D3. When we calculate the slope of the phase delay bx against the square root of the angular frequency w, we can estimate the depth information independent of the heat capacity inside the integrated circuit S, the amount of heat generation, and the position, which is determined by the shift component D2 determined by the depth of the heat generation point, while eliminating the phase offset component D3.

The integrated circuit failure analysis device 1 and the heat generation point detection method using the same as described above include detecting the heat generation detection signal in response to the application of the low-frequency bias voltage and detecting the heat generation detection signal in response to the application of the high-frequency bias voltage, from the integrated circuit S. Then detected are the phase shift between the low-frequency bias voltage and the heat generation detection signal and the phase shift between the high-frequency bias voltage and the heat generation detection signal and, the depth information of the heat generation point is obtained from the change rate of the phase shift against the square root of the frequency. This procedure results in calculating the depth information while cancelling out the offset component in the temporal change of the amount of heat generation varying depending upon the position of the heat generation point, whereby the depth information is obtained with high accuracy, independent of the position of the heat generation point. Moreover, by obtaining the change rate of the phase shift against the variable calculated from the frequency of the bias voltage, we can also obtain the depth information independent of the amount of heat generation at the heat generation point, the internal structure of the integrated circuit, and the frequency of the bias voltage.

Namely, the phase delay bx between the bias voltage and the heat generation detection signal involves deformation of the heat generation detection waveform dependent on the quantity of heat from the heat generation source, the position of the heat generation point in the integrated circuit S, the internal structure and the heat capacity of the integrated circuit, and so on, and thus includes variation associated therewith. Therefore, direct evaluation of the phase delay bx leads to failure in calculating an accurate depth of the heat generation point. For example, even if a parameter is one allowing us to calculate an accurate depth as long as the measurement is carried out in the center of the integrated circuit S, a significant error is made by directly applying the parameter to the measurement at the sample edge. The error of this kind is made by a difference of heat transfer rate and a difference of the sum of heat capacity in a heat transferred range. Specifically, it varies as shown in FIG. 4, with increase of heat capacity and increase of heat transfer rate. In the phase delay bx, the shift component D3 due to the deformation of the response waveform is produced from the minimum 0° to the maximum 90°, in addition to the shift component D2 corresponding to the phase delay from the heat generation source. This component becomes an extra offset, which has made the calculation of accurate depth difficult heretofore. The present embodiment allows us to obtain the accurate depth information while removing such extra offset.

Since the amplitudes and duty ratios of the bias voltages of multiple frequencies applied to the integrated circuit S are set to be equal to each other, the amounts of heat generation at the heat generation point can be made more uniform and the dependency of the depth information on the frequency of the bias voltage can be reduced more. As a result, much more accurate depth information can be acquired.

The present invention is by no means limited to the above-described embodiment. For example, the waveforms of the bias voltages applied to the integrated circuit S do not have to be limited to the rectangular waves, but may be other waveforms of voltages fluctuating periodically, like sinusoidal waves or triangular waves.

The maximum $V_1$ and minimum $V_2$ of the bias voltages may also be suitably changed according to a type of the integrated circuit S. However, when a plurality of frequencies are used as changed for one integrated circuit S, it is preferable to set the maximum $V_1$ and minimum $V_2$ constant.

Since an increase or a decrease of the frequency of the bias voltage leads to variation in amplitude of the heat generation detection signal, it is necessary to keep the amplitude at the lowest frequency to be measured, within a measurable range. Then, the integrated circuit failure analysis device 1 may be provided with a function to automatically detect an event of the amplitude of the heat generation detection signal exceeding the measurable range and output an error.

The fourth step is preferably to calculate the change rate of the phase shift against the variable which is the square root of the frequency. This allows us to obtain higher-accuracy depth information, independent of the position of the heat generation point, the amount of heat generation, the internal structure of the integrated circuit, and the frequency of the periodic electric signal.

It is also preferable that the duty ratios of the periodic electric signals supplied in the first step and the second step be equal to each other. In this case, the amounts of heat generation at the heat generation point can be made more uniform, whereby the dependency of the depth information on the frequency of the periodic electric signal can be reduced more.

It is preferable that the synchronism control unit 15 set and control each of the maximum voltage $V_1$ and the minimum voltage $V_2$ of the low-frequency and high-frequency bias voltages so that the duty ratios in the predetermined durations of the periodic electric signals supplied in the first step and the second step become equal to each other. This makes the amount of heat generation in the low-frequency bias voltage application period approximately equal to the amount of heat generation in the high-frequency bias voltage application period, and thus it becomes feasible to apply the low-frequency bias voltage and the high-frequency bias voltage in series, with expectations of reduction of measurement time and improvement in measurement accuracy.

INDUSTRIAL APPLICABILITY

The present invention is applicable to the heat generation point detection methods and heat generation point detection devices for detecting the depth of the heat generation point in the integrated circuit and allows accurate detection of the depth of the heat generation point in the integrated circuit, independent of the condition and position thereof.

REFERENCE SIGNS LIST 1 integrated circuit failure analysis device; 14 voltage application unit (electric signal supply unit); 18 imaging device; 20 control unit; 21 imaging control unit; 22 stage control unit; 23 synchronism control unit; 30 image processing unit; 31 image storage unit; 32 heat generation signal acquisition unit (detection unit); 33 voltage phase acquisition unit; 34 phase delay acquisition unit (phase shift detection unit); 35 depth information calculation unit; S integrated circuit.

The invention claimed is:
1. A method for acquiring a depth of a heat generation point in an integrated circuit, comprising:
supplying a first electric signal at a first frequency to the integrated circuit;

acquiring a first detection signal indicative of a change of an amount of heat generation detected from the integrated circuit in response the first electric signal;

acquiring a first phase shift between the first electric signal of the first frequency and the first detection signal and a first variable which is the square root of the first frequency;

supplying a second electric signal at a second frequency different from the first frequency, to the integrated circuit;

acquiring a second detection signal indicative of a change of an amount of heat generation detected from the integrated circuit in response the second electric signal;

acquiring a second phase shift between the second electric signal of the second frequency and the second detection signal and a second variable which is the square root of the second frequency; and acquiring depth information, x, of the heat generation point indicating the depth of the heat generation point in the integrated circuit, on the basis of a variation of the phase shift, dbx, between the first phase shift and the second phase shift, and a variation of the variable, $df^{1/2}$, between the first variable and the second variable using the following equation:

$$\frac{dbx}{d\sqrt{f}} = x\sqrt{\frac{\rho q \pi}{k}},$$

wherein ρ is the density of the integrated circuit material, q is the specific heat of the integrated circuit material, and κ is the heat transfer coefficient of the integrated circuit material.

2. The method according to claim 1, wherein duty ratios of the first electric signal are set to be equal to duty ratios of the second electric signal.

3. An apparatus for acquiring a depth of a heat generation point in an integrated circuit, comprising:
an electric signal supply unit configured to supply an electric signal to the integrated circuit;
a control unit configured to control the electric signal supply unit so as to supply a first electric signal at a first frequency and a second electric signal at a second frequency different from the first frequency, to the integrated circuit;
a detection unit configured to acquire a first detection signal indicative of a change of an amount of heat generation detected from the integrated circuit in response to supply of the first electric signal and configured to acquire a second detection signal indicative of a change of an amount of heat generation detected from the integrated circuit in response to supply of the second electric signal;
a phase shift detection unit configured to acquire a first phase shift between the first electric signal and the first detection signal and a second phase shift between the second electric signal and the second detection signal; and
a calculation unit configured to acquire a first variable which is the square root of the first frequency and a second variable which is the square root of the second frequency and acquire depth information, x, of the heat generation point indicating the depth of the heat generation point in the integrated circuit, on the basis of a variation of the phase shift, dbx, between the first phase shift and the second phase shift, and a variation of the variable, $df^{1/2}$, between the first variable and the second variable using the following equation:

$$\frac{dbx}{d\sqrt{f}} = x\sqrt{\frac{\rho q \pi}{k}},$$

wherein ρ is the density of the integrated circuit material, q is the specific heat of the integrated circuit material, and κ is the heat transfer coefficient of the integrated circuit material.

4. A method for acquiring a depth of a heat generation point in an integrated circuit, comprising:
supplying a plurality of electric signals to the integrated circuit;
acquiring a plurality of detection signals indicative of a change of an amount of heat generation detected from the integrated circuit in response to the plurality of electric signals;
acquiring a plurality of phase shifts between one of the plurality of electric signals and one of the plurality of detection signals that corresponds to the on of the plurality electric signals and a plurality of variables which are values of the square root of the frequencies of the plurality of electric signal; and
acquiring depth information, x, of the heat generation point indicating the depth of the heat generation point in the integrated circuit on the basis of a variation of a phase shift, dbx, against a first of the plurality of phase shifts and a second of the plurality of phase shifts, and a variation of the variable, $df^{1/2}$, between the first of the plurality of variables and the second of the plurality of variables using the following equation:

$$\frac{dbx}{d\sqrt{f}} = x\sqrt{\frac{\rho q \pi}{k}},$$

wherein ρ is the density of the integrated circuit material, q is the specific heat of the integrated circuit material and κ is the heat transfer coefficient of the integrated circuit material.

5. The method according to claim 1, wherein the first detection signal and the second detection signal are acquired on the basis of a plurality of heat generation images which is acquired in time series by using an imaging device.

6. The method according to claim 5, wherein a frame rate of the imaging device is set on the basis of the first frequency or the second frequency.

7. The method according to claim 1, wherein the first frequency and the second frequency are set to no more than 10 Hz.

8. The method according to claim 1, wherein the first phase shift and the second phase shift are acquired by using a lock-in detector.

9. The apparatus according to claim 3, wherein duty ratios of the first electric signal are equal to duty ratios of the second electric signal.

10. The apparatus according to claim 3, wherein the detection unit comprises an imaging device configured to acquire in time series a plurality of heat generation images and configured to acquire the first detection signal and the second detection signal on the basis of the plurality of heat generation images.

11. The apparatus according to claim 10, wherein a frame rate of the imaging device is set on the basis of the first frequency or the second frequency.

12. The apparatus according to claim 3, wherein the first frequency and the second frequency are set to no more than 10 Hz.

13. The apparatus according to claim 3, wherein the phase shift detection unit configured to detect the first phase shift and the second phase shift by lock-in detection.

14. An apparatus for acquiring a depth of a heat generation point in an integrated circuit, comprising:
   an electric signal supply configured to supply a plurality of electric signals to the integrated circuit;
   a detection unit configured to acquire a detection signal indicative of a change of an amount of heat generation detected from the integrated circuit in response each of the electric signals;
   a phase shift acquisition unit configured to acquire a phase shift between the electric signal and the detection signal and a variable which is the square root of the frequency of the electric signal; and
   a calculation unit configured to acquire depth information of the heat generation point, x, indicating the depth of the heat generation point in the integrated circuit, on the basis of a variation of the phase shift, dbx, between the first phase shift and the second phase shift, and a variation of the variable, $df^{1/2}$, between the first variable and the second variable using the following equation:

$$\frac{dbx}{d\sqrt{f}} = x\sqrt{\frac{\rho q \pi}{k}},$$

wherein $\rho$ is the density of the integrated circuit material, q is the specific heat of the integrated circuit material, and $\kappa$ is the heat transfer coefficient of the integrated circuit material.

* * * * *